United States Patent
Kennedy et al.

(10) Patent No.: US 6,669,949 B2
(45) Date of Patent: Dec. 30, 2003

(54) SILOXANE-CONTAINING OIL COMPOSITIONS WITH GOOD SPREADING PROPERTIES

(75) Inventors: Wayne Kennedy, Glen Allen, VA (US); Arno Knebelkamp, Essen (DE); Peter Lersch, Dinslaken (DE); Jörg Simpelkamp, Richmond, VA (US); Stephen Wilkowski, Richmond, VA (US)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 09/881,340

(22) Filed: Jun. 14, 2001

(65) Prior Publication Data

US 2001/0039321 A1 Nov. 8, 2001

Related U.S. Application Data

(62) Division of application No. 09/536,186, filed on Mar. 24, 2000, now abandoned.

(51) Int. Cl.$^7$ ................................................ A01N 25/04
(52) U.S. Cl. .................... 424/405; 528/14; 528/37; 528/31; 528/15; 528/26; 528/29; 556/444; 556/479; 556/451; 556/445; 568/673; 568/675; 523/105; 504/116.1
(58) Field of Search .............................. 528/14, 37, 31, 528/15, 29, 25; 556/444, 479, 451, 445; 568/673, 675; 504/116.1; 523/105; 424/405

(56) References Cited

U.S. PATENT DOCUMENTS

| | | |
|---|---|---|
| 4,514,319 A | 4/1985 | Kulkarni et al. |
| 4,990,175 A | 2/1991 | Petroff et al. |
| 5,025,074 A | 6/1991 | Davis et al. |
| 5,132,047 A | 7/1992 | Tanaka et al. |
| 5,145,915 A | 9/1992 | Weitemeyer et al. |
| 5,204,438 A | 4/1993 | Snow et al. |
| 5,244,599 A | 9/1993 | Terse et al. |
| 5,271,868 A | 12/1993 | Azechi et al. |
| 5,391,679 A | 2/1995 | Burkhart et al. |
| 5,484,950 A | 1/1996 | Crivello |
| 5,556,902 A | 9/1996 | Shouji et al. |
| 5,558,806 A | 9/1996 | Policello et al. |
| 5,645,842 A | 7/1997 | Gruning et al. |
| 5,658,851 A | 8/1997 | Murphy et al. |
| 5,658,852 A | 8/1997 | Murphy et al. |
| 5,691,392 A | 11/1997 | Okorofor |
| 5,831,110 A | 11/1998 | Isoda et al. |
| 6,300,283 B1 * | 10/2001 | Sakuta |

FOREIGN PATENT DOCUMENTS

WO    WO 97032475 A    9/1997

OTHER PUBLICATIONS

Holohan et al., *Monofunctional polydimethylsiloxane oligomers for graft copolymerisation,* Macromol. Chem. Phys. 195, 2965–2979 (1994);.

Chemical Abstracts, vol. 123: 199789, abstract of JP 07–171 276 (1995).

Chemical Abstracts, vol. 121: 84332, abstract of JP 06–016 814 (1994).

* cited by examiner

*Primary Examiner*—Robert Dawson
*Assistant Examiner*—Kuo-Liang Peng
(74) *Attorney, Agent, or Firm*—Frommer Lawrence & Haug LLP

(57) ABSTRACT

This invention relates to asymmetrical, substituted polysiloxanes which show good compatibility in a variety of oils and improve the spreading behavior of oil-based formulations, to a process for preparing these asymmetrical polysiloxanes and to oil formulations containing said asymmetrical polysiloxanes. The asymmetrical polysiloxanes of this invention are used in herbicidal and pesticidal compositions, in cosmetic and pharmaceutical preparations as well as in industrial applications. The assymmetrical substituted polysiloxanes have the following formula (II)

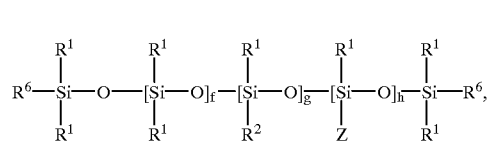

wherein $R^1$, $R^2$, Z a and b are described herein.

14 Claims, No Drawings

SILOXANE-CONTAINING OIL COMPOSITIONS WITH GOOD SPREADING PROPERTIES

RELATED APPLICATIONS

This application is a divisional of application U.S. Ser. No. 09/536,186, filed on Mar. 24, 2000, now abandoned, herein incorporated by reference.

FIELD OF THE INVENTION

This invention relates to asymmetrical, substituted polysiloxanes which show good compatibility in a variety of oils and improve the spreading behavior of oil-based formulations to a process for preparing these asymmetrical polysiloxanes and to oil formulations containing said asymmetrical polysiloxanes. The asymmetrical polysiloxanes of this invention are used in herbicidal and pesticidal compositions, in cosmetic and pharmaceutical preparations as well as in industrial applications.

BACKGROUND OF THE INVENTION

It is well known that polysiloxanes can improve the spreading of oils on the surfaces of, for example, human skin, the waxy leaf cuticle of plants, and plastics. This class of compounds achieves this result by reducing the bulk surface tension of the preparation so that the oil-based formulation can spread over hydrophobic surfaces. Oils are generally used in the preparation of creams and lotions in cosmetic and pharmaceutical preparations. Oils also have utility in the field of tribology. Oils are also used as pesticides, herbicides adjuvants for spray mixes, or carriers for herbicides.

The reason for this is because many of the herbicides and pesticides have limited water solubility and the oils function as carriers to deliver the active ingredient to the target plant or pest. The spreading and solubilizing characteristics of these oils improve the coverage and penetration of the active ingredients into the hydrophobic surface of the target organisms. The oils used in the present compositions can also function as insecticides in their own right. Petroleum and vegetable oils are used to control infestations of insects and mite. These oils act as suffocants which interfere with the respiratory process of the arthropod. The oils exert this activity by clogging the spiracles of the insect or mite.

Oils possess good spreading and wetting properties on waxy surfaces because of their inherently low surface tension. The spreading ability of an oil-based preparation can be increased even further by adding adjuvants which modify the surface tension of the oil. For example, Schaefer in an article titled "Tenside Surfactants Detergents" in the *Journal for Theory Technology and Application of Surfactants*, April 1994, describes the use of silicone waxes to reduce the surface tension of mineral oil. These silicone waxes lower the surface tension of the organic system by reducing the surface tension of mineral oils, thereby improving the ability of the preparations to spread. As a rule, however, the spreading ability of mixtures of oils and silicone waxes is only slightly better than that of pure oils. Similarly, polysiloxanes are also used as agents to improve the spreading abilities of oils. The disadvantage of the use of these agents is the generally poor compatibility (solubility) of the polysiloxane with the oil especially when long segments consisting only of polydimethylsiloxane units are present since the solubility of the polysiloxane in the oil decreases as the number of dimethylsiloxy units increases.

This invention is concerned with organopolysiloxanes which exhibit good solubility in organic oils and have the ability to improve the ability of the oils to spread on a variety of surfaces including human skin, plants, metals, plastics and chitin.

DESCRIPTION OF THE RELATED ART

Certain Materials are known in the art to reduce the surface tension of oils. Besides silicone waxes, silicone copolymers are known to enhance the spreading properties of cosmetic emollients, oils and waxes as described by Floyd, Sarnecki and Macpherson in *Soaps, Perfumeries and Cosmetics*, vol. 69, p 26 (March 1996).

In U.S. Pat. No. 4,514,319, Kulkarni, et al. disclose antifoam compositions that utilize alkyl and polyether functional silicones as a means to reduce the surface tension of hydrocarbon oils when they are used in connection with organo-silicone surfactants.

Grüning, et al. in U.S. Pat. No. 5,645,842, herein incorporated by reference, disclose cosmetic or pharmaceutical preparations which use organopolysiloxanes to increase the spreading behavior of oils which contain ester groups. The organopolysiloxanes used in the preparation were modified with long-chain alkyl or alkoxy groups.

Murphy, et al., in U.S. Pat. No. 5,561,009 disclose that one can increase the spreading properties of oil-containing composition by adding to the composition a linear alkylsilicone of the formula

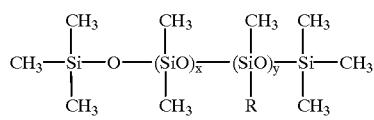

or a cyclic alkylsilicone compound

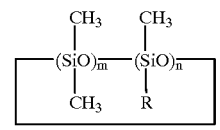

where x is an integer form 0 to 20, m is an integer from 0 to 4, n is from 1 to 5 provided that m+n is from 3 to 5, and R is an alkyl group Those alkylsilicone compounds are used as adjuvants in preparing agricultural formulations which contain mineral or vegetable oils U.S. Pat. No. 5,658,851, also to Murphy, et al., discloses lipophilic siloxanes which decrease the surface tension of oils. Those siloxanes have the following general formula

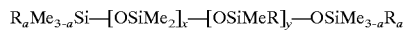

where R is a lipophilic group selected from the group consisting of aryl, substituted aryl, aralkyl, alkyl phenyl ether, substituted phenylether, or alkyl alkyleneoxide groups; a is 0 or 1; x and y is 0 to 4 depending upon a, provided that the sum of x and y is greater than or equal to 6. Those siloxanes are taught to be adjuvants in oil-based herbicidal, fungicidal, or insecticidal compositions However, the ability of the polysiloxanes known in the art to spread oils is not always satisfactory. Furthermore, polysiloxane compounds which improve spreading of one specific oil often lack the compatibility with other oils which are used according to the state of the art. Hence there is a need to develop novel polysiloxane compounds with improved spreading properties and high compatability with a wide range of natural and synthetic oils to be used in oil-based formulations.

Object of the Invention

An object of this invention is, therefore, to develop a new class of organopolysiloxanes with improved compatability with a wide range of natural and synthetic oils, a process to prepare these compounds and their use. Another object of this invention is the preparation of compositions comprising natural or synthetic oils and this new class of organopolysiloxanes, optionally with additional organo-modified silicone copolymers, which possess enhanced spreading properties relative to the oil itself, and their use. These objectives are achieved using asymmetrical polysiloxanes with superior compatability in a wide variety of natural and synthetic oil compositions, imparting an excellent spreading behaviour.

SUMMARY OF THE INVENTION

This invention relates to asymmetrically substituted polysiloxanes of the formula

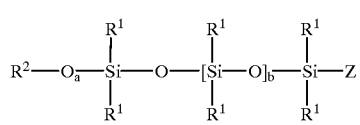

(I)

wherein $R^1$ and $R^2$ are same or different and represent linear or branched, substituted or unsubstituted, saturated or unsaturated alkyl or aryl groups with 1 to 32 carbon atoms which optionally interrupted by oxygen atoms in the hydrocarbon chains, Z is a polyoxyalkylene radical of the structure

wherein $R^3$ represents the same or different bivalent alkyl or aryl radicals with 1 to 30 carbon atoms, $R^4$ represents hydrogen and/or the same or different alkyl or aryl radicals with 1 to 30 carbon atoms, $R^5$ represents hydrogen and/or same or different, linear or branched alkyl, aryl or acyl radicals with 1 to 30 carbon atoms, which may be substituted with hydroxy groups, halogens, unsubstituted or substituted alkyl, aryl, alkyloxy or aryloxy groups with 1 to 24 carbon atoms, k equals 0 or 1, l equals 0 or 1,
m equals 0 or 1,
n equals 2 or 4,
o equals values from 1 to 100;
a equals 0 or 1, and
b equals 0 to 200;

their use in oil compositions with improved spreading properties, and a process to prepare these compounds.

This invention also provides for oil-based compositions having improved spreading properties and compatability which comprise 99.9% to 50% by weight of one or several oils; and 0.01% to 50% by weight of an organosilicone composition comprising asymmetrically substituted polysi loxanes according to formula (I) and optionally one or several symmetrical polysiloxanes according to the formula (II)

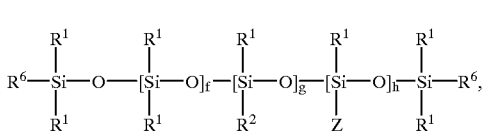

(II)

wherein $R^1$, $R^2$ and Z assume the meaning mentioned above, $R^6$ assumes the meaning of $R^1$, $—O_a—R^2$ or that of Z, f, g and h can be 0 to 200, a can be 0 or 1, and which may optionally contain branching units of the structure $[R^6SiO_{3/2}]$. The residues $R^1$, $R^2$ and Z in the siloxanes (II) can be the same or different as the residues $R^1$, $R^2$ and Z in the asymmetrical siloxanes (I).

This invention also relates to oil compositions containing the asymmetrically substituted organosilicones described in this invention for use in personal care, pharmaceutical, agricultural and in industrial applications, or as processing aids in the paper, plastics and metallurgical industry.

Preferred residues $R^1$ are alkyl groups with 1 to 4 carbon atoms or phenyl, especially preferred is methyl. Preferred residues $R^2$ are same or different, linear or branched alkyl groups with 6 to 24 carbon atoms, for example linear or branched hexyl, octyl, decyl, nonyl, undecyl, dodecyl, tetradecyl, hexadecyl or octadecyl groups, alkyl substituted aryl groups like nonyl phenyl, arylsubstituted alkyl groups like phenylethyl. Especially preferred are alkyl groups with 10 to 18 carbon atoms.

Residue $R^5$ represents hydrogen and/or same or different, linear or branched alkyl, aryl or acyl radicals with 1 to 30 carbon atoms, preferred 1 to 12 carbon atoms, which may be substituted with hydroxy groups, halogens, or alkyl, aryl, alkyloxy or aryloxy groups with 1 to 24 carbon atoms which are unsubstituted or substituted, for example with halogen, alky, aryl, alkoxy, alkylamino groups.

Preferred residues Z are same or different polyalkylene oxides wherein $R^3$ represents bivalent alkyl radicals with 2 or 3 carbon atoms, k and l equals 1, m equals 0 or 1, n equals 2, o equals 5 to 100, $R^4$ is from the group of hydrogen, methyl, ethyl or phenyl, $R^5$ represents hydrogen, methyl, $C_1$–$C_{18}$ acyl, or alkylsubstituted phenyl.

Especially preferred residues Z are polymers of ethylene oxide, propylene oxide or mixtures thereof, wherein $R^3$ is propyl, $R^4$ is hydrogen or methyl, l equals 1, m equals 0 or 1, n equals 2, o equals 8 to 60 and $R^5$ is hydrogen, methyl, acetyl, octylphenyl or nonylphenyl groups.

Preferred siloxane chain lengths range from values of b=1 to 100. Especially preferred values of b range from 10 to 60. Preferred value of a is 0.

The polysiloxanes of formula (I) can be prepared by reacting a cyclic siloxane, e.g. hexamethyltrisiloxane with an organometallic compound, e.g. an alkyllithium compound $R^2Li$, and subsequently reacting the product thus formed with dimethylchlorosilane to form an asymmetrical siloxane with one terminal alkyl and one terminal Si—H group, followed by hydrosilylation with an unsaturated polyalkylene oxide derivative. The anionic ring-opening polymerisations of cyclic siloxanes with alkyllithium compounds is well known in the state of the art, as is the reaction of the intermediate anion with dimethylchlorosilane. Asymmetrical siloxanes, having only one terminal SiH group, have been synthesized and hydrosilylated, for example, with allyl and vinyl phenols, as described in U.S. Pat. Nos.

5,025,074 or 5,204,438, or with vinyl silanes, as described in U.S. Pat. No. 5,075,349.

The alkyllithium reagents for this reaction are well known to one skilled in this art. These reagents are either commercially available or are prepared using various processes according to the state of the art, including metal-halogen exchange, reacting the appropriate alkyl halide with the lithium metal. For a general discussion of these processes, see F. A. Carey and R. J. Sundberg, "Advanced Organic Chemistry", 2nd. Ed., pp. 249–257, Plenum Press, New York (1983) and J. March, "Advanced Organic Chemistry", 3rd ed., pp. 556–561, John Wiley & Sons, New York (1985).

The hydrosilylation reaction and the unsaturated polyoxyalkylene derivatives are well known in the art. The reaction conditions and catalysts employed have been described in detail, for example, by W. Noll in "Chemie und Technologie der Silicone", 2nd ed., Verlag Chemie, Weinheim (1968), by B. Marciniec in "Appl. Homogeneous Catal. Organomet. Compd. 1996, 1, 487)" or by G. C. Davis et al. in U.S. Pat. No. 5,204,438, and are incorporated herein by reference.

Unsaturated polyoxyalkylene derivatives can, for example, have the structure (V)

$$A-O_l(C_nH_{2n-m}R^4{}_mO)_oR^5 \qquad (V),$$

wherein $R^4$, $R^5$, l, m, n and o have the meaning defined above and A is an unsaturated carbon radical with two to 30 carbon atoms, for example unsaturated alkyl groups with terminal double or triple bonds, like vinyl or allyl. Especially preferred are unsaturated polyethers wherein A is allyl, $R^4$ is hydrogen or methyl, 1 equals 1, m equals 0 or 1, n equals 2, o equals 8 to 60 and $R^5$ is hydrogen, methyl, acetyl, octylphenyl or nonylphenyl group.

The asymmetrical polysiloxanes show improved compatability with a wide variety of natural and synthetic oils.

This invention also relates to oil-based formulations comprising an oil composition having improved spreading properties. This oil composition comprises 99.9% to 50% by weight of one or several oil and 0.01% to 50% by weight of an organosilicone composition comprising asymmetrically substituted polysiloxanes according to formula (I) and, optionally, one or several symmetrical polysiloxanes of formula (II).

Preferred compounds of formula (II) are symmetrical siloxanes of the structure:

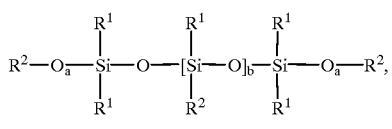

(III)

and

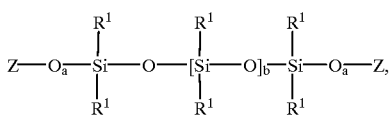

(IV)

wherein $R^1$, $R^2$, Z, a and b are as defined above. A preferred compound of the structure (IV) is one wherein b has a value of 5 to 80 and Z represents a radical with the structure

$$R^9-(C_6H_4)-O-(C_2H_4O-)_d(C_3H_6O)_e-$$

wherein $R^9-(C_6H_4)$ are alkyl phenyl groups with $R^9$ representing octyl or nonyl, d is 0 and e is 5 to 80.

It is preferred that the organosilicone composition does not contain more than 40% by weight, especially preferred no more than 30% by weight, of each of the symmetrical polysiloxanes (II).

Preferred are compositions comprising 90% to 99.9% by weight of oil and 0.1% to 10% by weight of the organosilicone composition. Especially preferred are organosilicone compositions which contain 30% to 100% by weight of the asymmetrical polysiloxane of formula (I) and 0% to 70% by weight of one or several symmetrical polysiloxanes of formula (II), the organosilicone composition preferably not containing more than 40% by weight of each single component of formula (II). Especially preferred are organosiloxane compositions which contain 50% to 100% by weight of the asymmetrical polysiloxane of formula (I) and 0% to 50% by weight of symmetrical polysiloxanes of formula (11), the organosilicone composition preferably not containing more than 30% by weight of each single component of formula (II). Most preferred are organosiloxane compositions which contain 90% to 100% by weight of the asymmetrical polysiloxane of formula (I) and 0% to 10% by weight of symmetrical polysiloxanes of formula (II).

The positive effect of the asymmetrical polysiloxanes can be seen even in organosiloxane compositions according to this invention which comprise 50% by weight of an asymmetrical siloxane (I), and 50% by weight of a mixture of symmetrical siloxanes (II) and (IV). These mixtures have significantly improved properties compared to simple mixtures of (III) and (IV) alone. They can be prepared, for example, by sequential or simultaneous hydrosilylation of an α,ω-SiH functional siloxane with an α-olefin and an unsaturated polyoxyalkylene compound, e.g. of the structure $CH_2=CH-CH_2-O-(C_nH_{2n-m}R^4{}_mO)_oR^5$ wherein $R^4$, $R^5$, m, n, o have the meaning defined above, in the presence of a platinum catalyst; or by equilibration reaction of an symmetrical siloxane (III) and an symmetrical siloxane (IV) in the presence of equilibration catalyst according to the state of the art; or by equilibration of a symmetrical siloxane (III) with an α,ω-SiH-functionalized siloxane and subsequent hydrosilylation with an unsaturated polyoxyalkylene compound; or by equilibration of a symmetrical siloxane (IV) with an α, ω-SiH-functionalized siloxane and subsequent hydrosilylation with an unsaturated α-olefin. The equilibration reaction is a reaction well known to the practitioner of the art and is described, for example, in W. Noll: "Chemie und Technologie der Silicone", 2nd ed, Verlag Chemie, Weinheim (1968) Equilibration catalysts according to the state of the art, comprise, for example basic catalysts like alkali metal or tetraalkyl ammonium hydroxides or alkoxides, acidic or Lewis acidic catalysts like organic or inorganic acids such as sulfuric acid, sulfonic acids, solid-phase catalysts like minerals, clays or ion exchanger resins, or phosphornitrile chlorides and its derivatives.

Symmetrical organo-modified siloxanes (II) are well known in the art, and have been used in cosmetic or defoamer compositions, for example, see WO 99/18784 to Carr et al., EP 596304 to Gruning et al., U.S. Pat. No. 5,271,868 to Azechi et al., U.S. Pat. No. 5,059,704 to Petroff et al., U.S. Pat. No. 5,244,599 to Terae et al., U.S. Pat. No. 4,514,319 to Kulkarni et al., U.S. Pat. No. 5,658,852 to Murphy et al. However, with respect to spreading properties and compatibility they are inferior to the compositions containing asymmetrical siloxanes of formula (I).

The oils contemplated by this invention are the commonly accepted paraffinic or aromatic-based mineral, animal or vegetable oils used in the cosmetic, pharmaceutical or agriculture arts. Especially preferred are methylated vegetable oils. Specific examples of oils include paraffinic, isoparaffinic and cycloparaffinic mineral oils, plant oils like soybean oil, canola oil, castor oil, palm oil, olive oil, corn oil, cottonseed oil, sesame seed oil and the like. In addition, methylated oils, such as methylated soybean oil, methyl palmitate, methyl oleate, and the like are also suitable carrier oils. Mixtures of mineral, vegetable and/or methylated oils may also be employed. The carrier oil may itself be an active ingredient, e.g., a pesticide. Exemplary mineral oils are those marketed under the trade names EXXOL®, ISOPAR®, NORPAR® and ORCHEX® from Exxon Chemical (Houston, Tex.). Methylated oils (from reacting oils with methanol) such as the methylated soybean oil are available from Henkel, Canada, under the product name "Emery 2235, Distilled Methylsoyate." The inventive compositions can be used in herbicidal, pesticidal, cosmetic and pharmaceutical preparations in order to produce oil-based preparations which possess enhanced spreading properties.

The cosmetic, industrial or pharmaceutical preparations can be used in the form of oils containing the asymmetrical polysiloxane of formula (I) and, optionally, symmetrical polysiloxane of formula (II), in the form of solutions or emulsions. The emulsions can be either creams or lotions and are present in the form of O/W or W/O emulsions. It is also possible to use these oils as carriers for active ingredients. Examples of active ingredients are pigments, sunscreens, fragrances, cosmetically and/or pharmaceutically active substances such as vitamin E or esters of nicotinic acid. Other active ingredients can be, for example, extreme pressure additives, corrosion inhibitors, inorganic particles like silica or $TiO_2$, waxes and others. Such preparations can optionally include auxiliaries like foam control agents, thickeners, emulsifiers and inert carriers which are customary in the cosmetic and pharmaceutical arts. The amount of active ingredient in these preparations is well known to a practitioner of this art. The term "herbicide" means any compound which is used to destroy unwanted plant growth. The term "pesticide" means any compound which destroys fungus, insects and rodents and the like. The term "pesticide" specifically includes oily materials which are otherwise not toxic but are used as suffocants in the destruction of aphids, mites and other insects. Illustrative examples of herbicides and pesticides which can be employed in the present invention include growth regulators, photosynthesis inhibitors, pigment inhibitors, mitotic disruptors, lipid biosynthesis inhibitors, cell wall inhibitors, and cell membrane disruptors. The amount of pesticide employed in compositions of the invention varies with the type of herbicide or pesticide employed and the specific amount and application rate is well known to the practice. However, such compositions generally contain about 1 to 99% of herbicide or pesticide although more or less active ingredients may be used. The following are representative, but nonlimiting examples of pesticide compounds that can be used in the compositions of the invention:

Growth Regulators

Phenoxy Acetic Acids, such as 2,4-D [(2,4-dichlorophenoxy)acetic acid];
Phenoxy Propionic Acids, such as Dichlorprop[(RS)-2-(2,4-dichlorophenoxy) propionic acid], Mecoprop [(RS)-2-(4-chloro-o-tolyloxy)-propionic acid];
Phenoxy Butyric Acids, such as 2,4-DB[4-(2,4-Dichlorophenoxy)butyric acid];
Benzoic Acids, such as Dicamba [3,6-dichloro-o-anisic];
Other growth regulators, such as Fluroxypyr [4-amino-3,5-dichloro-6-fluoro-2-pyridyloxy-acetic acid], Picloram [4-amino-2,3,5-trichlor-2-carboxylic acid], Triclopyr [3,5,6-trichloro-2-pyridyloxyacetic acid], Copyralid [3,6-dichloropyridine-2-carboxylic acid];

Pigment Inhibitors: such as Amitrole, [1H-1,2,4-triazol-3-ylamine; 3-amino-1H-1,2,4triazole], Clomazone [2-(2-chlorobenzyl)4,4-dimethyl-1,2-oxazolidin-3-one;2-(2-chlorobenzyl)4,4-imethylisoxazolidin-3-one], Fluridone [1-methyl-3-phenyl-5-(a,a,a-trifluoro-m-tolyl)4-pyridone], Norflurazone [4-chloro-5-methylamino-2-(a,a,a-trifluoro-m-tolyl)pyridazin-3(2H)-one];

Mitotic disruptors: Dinitroanilines, such as Isopropalin [4-isopropyl-2,6-dinitro-N,N-dipropylaniline], Oryzalin [3,5-dinitro-N4N4-dipropylsulfanilamide], Pendimethalin [N-(1-ethylpropyl)-2,6-dinitro-3,4-xylidine], Prodiamine [5-dipropylamino-a,a,a-trifluoro4,6-dinitrotoluidine; 2,6-dinitro-N1N1-dipropyl-4-trifluoromethyl-m-phenylenediamine], Trifluralin [a,a,a-trifluoro-2,6-dinitro-N,N-dipropyl-p-toluidine];

Inhibitors of lipid biosynthesis, such as Clethodim [(±)-2-[(E)-3-chloroallyloxyimino]propyl]-5-[2(ethylthio)-propyl]-3-hydroxycyclohex-3-enone], Diclofop-methyl [(RS)-2-[4-(2,4-dichlorophenoxy)phenoxy]propionic acid], Fenoxaprop-ethyl [(±)-2-[4-(6-chloro-1,3-benzoxazol-2-yloxy)phenoxy]propionic acid; (±)-2-[4-(5-chlorobenzoxazol-2-yloxy)phenoxy]propionic acid], Fluazifop-P-butyl [(R)-2-[4-(5-trifluoromethyl-2-pyridyloxy)phenoxy)propionic acid, Haloxyfop-methyl [(RS)-2-(4-(3-chloro-5-trifluoromethyl 2-pyridyloxy)phenoxy]propionic acid], Quizalofop[(RS)-2[4-(6-chloroquinoxalin-2-yloxy)phenoxy]propionic acid], Sethoxydim[.(±)-(EZ)-2-(1-ethoxyininobutyl)-5-[2(ethylthio)-propyl]-3-hydroxycyclohex-2-enone];

Photosynthesis Inhibitors

Triazines and s-Triazines such as Hexazinone [3-cyclohexyl-6-dimethylamino-1-methyl-1,3,4triazine-2,4(1H,3H)-dione], Metribuzin [4-amino-6-tert-butyl-3-methylthio-1,2,3-triazine-5(4H)-one], Atrazine [6-chloro-N2-ethyl-N4-isopropyl-1,3,5-triazine-2,4-diamine], Simazine [6-chloro-$N^2N^4$-diethyl-1,3,5-triazine-2,4diamine], Cyanazine 2-[4-chloro-6-ethylamino-1,3,5-triazin-2-yl]amino]-2-methylpropanenitrile, Prometon [$N^2,N^2$4-di-isopropyl-6-methoxy-1,3,5-triazine-2,4, diamine], Ametryn [$N^2$-ethyl-$N^4$-isopropyl-6-methylthio-1,3,5-triazine-2,4-diamine];

Substituted ureas, such as Diuron [3-(3,4-dichlorophenyl)-1,1-dimethylurea], Fluometuron [1,1-dimethyl-3-(a,a,a-trifluoro-m-tolyl)urea], Linuron [3-(3,4-dichlorophenyl)-1-methoxy-1-methylurea], Tebuthiuron [1-(5-tert-butyl,1,3,4-thiadiazol-2-yl)-1,3-dimethylurea], Uracils, such as Bromacil [5-bromo-3-sec-butyl-6-methyluracil], Terbacil [3-tert-butyl-5-chloro-6-methlyuracil];

Other photosynthesis inhibitors, such as Bentazon [3-isopropyl-1H-2,1,3-benzothiadiazin-4(3H)-one 2,2-dioxide], Desmedipham [ethyl 3'-phenylcarbamoyloxycarbanilate; ethyl 3-phenylcarbamoyloxyphenylcarbamate; 3-ethoxycarbonyl-aminophenyl phenylcarbamate], Methazole [2-(3,4-dichlorophenyl)-4-methyl-1,2,4-oxadiazolidine-3,5-dione], Phenmedipham [methyl 3-(3-methylcarbaniloyloxy) carbanilate, 3-methoxycarbonylaminophenyl 3'-methylcarbanilate], Propanil [3',4'-dichloropropionanilide], Pyridate [6-chloro-3-phenylpyridazin-4-yl S-octyl thiocarbonate];

Inhibitors of amino acid synthesis, such as Glyphosate [N-(phosphonomethyl)glycine], Sulfonylureas, such as Bensulfuron [a-(4,6-dimethoxypy-rimidin-2- ylcarbamoylsulfamoyl)-o-toluic acid], Chlorimuron [2-(4-chloro-6-methoxypyrimidin-2-ylcarbamoylsulfamoyl) benzoic acid], Chlorsulfuron [1-(2-chlorophenylsulfonyl)-3-(4-methoxy-6-methyl-1,3,5-triazin-2-yl)urea], Metsulfuron [2-(4-methoxy-6-methyl-1,3,5-triazin-2-ylcarbamoylsulfamoyl)benzoic acid], Nicosulfuron [2-(4,6-dimethoxypyrimidin-2-ylcarbamoylsulfamoyl)-N,N-dimethylnicotinamide; 1-(4, 6-dimethoxypyrimidin-yl)-3-(3-dimethylcarbamoyl-2-pyridylsulfonyl)urea], Primisulfuron [2-(4,6-bis (difluoromethoxy)pyrimidin-2-ylcarbamoylsulfamoyl)-benzoic acid], Sulfometuron [2-(4,6-dimethylpyrimidin-2-ylcarbamoylsulfamoyl)benzoic acid; 2-[3-(4,6-dimethylpyrimidin-2yl)ureidosulfonyl)3benzoic acid], Thifensulfuron [3-(4-kethoxy-6-methyl-1,3,5-triazin-2ylcarbamoylsulfamoyl)thiophen-2-carboxylic acid], Triasulfuron [1-(2-(2-chloroethoxy)phenylsulfonyl)-3(4-methoxy-6-methyl-1,3,5-triazin-2yl)urea], Tribenuron [2-(4-methoxy-6-methyl-1,3,5-triazin-2-yl(methyl) carbamoyl-sulfamoyl)benzoic acid], Imidazolinones, such as Imazamethabenz [a reaction product comprising(±)-6-(4-isopropyl-4methyl-5-oxo-2-imidazolin-2-yl)-m-toluic acid and (±)-2-(4-isopropyl4methyl-5-oxo-2-imidazolin-2-yl)-p-toluic acid], Imazapyr [2-(4-isopropyl-4-methyl-5-oxo-2-imidazolin-2yl)nicotinic acid], Imazaquin [(RS)-2-(4-isopropyl-4-methyl-5-oxo-2-imidazolin-2-yl)quinoline-3-carboxylic acid], Imazethapyr [(RS)-5-ethyl-2-(4-isopropyl-4-methyl-5-oxo2-imidazolin-2-yl)nicotinic acid];

Cell membrane disruptors: Bipyridylium compounds, such as Diquat [9,10-dihydro-8a-diazoniaphenanthrene; 6,7-dihydrodipyrido[1,2-a:2',1'-c]pyrazine-5,8-dium; 1,1'-ethylene-2,2'-bipyridyldiylium], Paraquat [1,1'-dimethyl4,4'-bipyridinium(I)], Diphenylethers, such as Acifluorfen [5-(2-chloro-a,a,a-trifluro-p-tolyoxy)-2-nitrobenzoic acid], Fomesafen [5-(2-chloro-a,a,a-trifluro-p-tolyloxy)-N-mesyl-2-nitrobenzamide; 5-(2-chloro-a,a,a-trifluoro-p-tolyoxy)-N-methylsulfonyl-2-nitrobenzamide], commercially available as REFLEX®, Lactofen [ethyl 0-(5-(2-chloro-a,a,a-trifluoro-p-tolyl-oxy)-2-nitrobenzoyl)-DL-lactate], Oxyfluorfen [2-chloro-a,a,a-trifluoro-p-tolyl 3-ethoxy-4-nitrophenyl ether];

Cell wall inhibitors like Dichlobenil [2,6-dichlorobenzonitrile], Isoxaben [N-[3-(1-ethyl-1-methylpropyl)-1,2-oxazol-5-yl]-2,6-dimethoxybenzamide; N[(3-(1-ethyl-1-methylpropyl)-isoxazol-5-yl]-2,6-dimethoxybenzarnide];

Other herbicides such as Glufosinate [4-(hydroxy(methyl) phosphinoyl]-DL-homoalanine; DL-homoalanin4-yl-(methyl)phosphinic acid], Bromoxynil, [3,5-dibromo-4-hydroxybenzonitrile];

3,5-dibromo-4-hydroxyphenyl cyanide, 2,6-dibromo-4-cyanophenyl octanoate].

Glyphosate is especially preferred as a herbicide.

The herbicidal and pesticidal preparations optionally contain the auxiliaries and inert carriers which are customary in the art. Such auxiliaries and inert carriers are well-known to the practitioner of the art, and include, for example, mineral oils, organic solvents or vegetable oils. Application and dosage rates are well known to the practitioner of this art.

EXAMPLES

Hexadecyllithium is prepared by reaction of 1-bromohexadecane with lithium metal. Anionic polymerization of cyclohexamethyltrisiloxane with the alkyllithium and the subsequent conversion with ClSiMe$_2$H to give the α,ω-monoalkylmonohydrogensiloxane is performed as described in U.S. Pat. No. 5,204,438.

Example 1: Hydrosilylation of Asymmetrical Hydrogen Siloxane

In a four-necked flask equipped with stirrer, thermometer, addition funnel and reflux condenser, inerted with nitrogen, a mixture of 61.6 g (0.12 mol) of an ethylene oxide-propylene oxide copolymer monoallyl ether (80 mol % propylene oxide, iodine value 50.9) and 0.04 g of hexachloroplatinic acid (10% w/w in isopropanol) are heated to 115° C. and 244 g of an α-hexadecyl-ω-SiH functional siloxane (0.041% w/w hydrogen) prepared acording to U.S. Pat. No. 5,204,438 are slowly added via the addition funnel. The reaction mixture is stirred at 120° C. and the reaction is monitored via the decrease of siloxane-bound hydrogen. The batch is kept at this temperature until the conversion is complete (3 hrs). The polysiloxane is mixed with Penreco Mineral Oil (Drakeol 10B LT 14109 K 9014) at a concentration of 5% w/w to give a clear oil composition with a dynamic surface tension of 24.0 dynes/cm.

Example 2: Synthesis of a Siloxane Composition Containing Asymmetrical Siloxanes In a four-necked flask equipped with stirrer, thermometer, addition funnel and reflux condenser, inerted with nitrogen, a mixture of 27.7 g (0.12 mol) 1-hexadecene and 61.6 g (0.12 mol) of an ethylene oxide-propylene oxide copolymer monoallyl ether (80 mol % propylene oxide, iodine value 50.9) and 0.08 g of hexachloroplatinic acid (10% w/w in isopropanol) are heated to 115° C. and 209 g of an α,ω-SiH functional siloxane (0.092% w/w hydrogen) are slowly added. The reaction mixture is stirred at 120° C. for one hour until the conversion is complete.

Example 3: Synthesis of a Siloxane Composition Containing Asymmetrical Siloxanes In a four-necked flask equipped with stirrer, thermometer, addition funnel and reflux condenser, inerted with nitrogen, a mixture of 20.4 g (0.09 mol) 1-hexadecene and 45.4 g (0.09 mol) of an ethylene oxide-propylene oxide copolymer monoallyl ether (80 mol % propylene oxide, iodine value 50.9) and 0.09 ml of hexachloroplatinic acid, 10% w/w in isopropanol, are heated to 115° C. and 213.8 g of an α,ω-SiH functional siloxane (0.066% w/w hydrogen) are slowly added. The reaction mixture is stirred at 120° C. for 1.25 h until the conversion is complete.

Example 4: Symmetrical Polyethersiloxane (Reference)

In a four-necked flask equipped with stirrer, thermometer, addition funnel and reflux condenser, inerted with nitrogen, 111.7 g of an ethylene oxide-propylene oxide copolymer monoallyl ether (80 mol % propylene oxide, iodine value 50.9) and 0.1 ml of hexachloroplatinic acid, 10% w/w in isopropanol, are heated to 115° C. and 188.2 g of an α,ω-SiH functional siloxane (0.092% w/w hydrogen) are added in 35 min. The reaction mixture is stirred at 120° C. for one hour until the conversion is complete.

Example 5: Symmetrical Polyethersiloxane (Reference)

In a four-necked flask equipped with stirrer, thermometer, addition funnel and reflux condenser, inerted with nitrogen, 70.4 g (0.14 mol) of an ethylene oxide-propylene oxide copolymer monoallyl ether (80 mol % propylene oxide, iodine value 50.9) and 0.08 ml of hexachloroplatinic acid, 10% w/w in isopropanol, are heated to 115° C. and 213.8 g of an α,ω-SiH functional siloxane (0.066% w/w hydrogen) are added in 40 min. The reaction mixture is stirred at 120° C. for one hour until the conversion is complete.

Example 6: Symmetrical Alkylsiloxane (Reference)

In a four-necked flask equipped with stirrer, thermometer, addition funnel and reflux condenser, inerted with nitrogen, a mixture of 63.3 g (0.28 mol) 1-hexadecene and 0.1 ml of hexachloroplatinic acid, 10% w/w in isopropanol, are heated to 115° C. and 213.8 g of an α,ω-SiH functional siloxane (0.092% w/W hydrogen) are added in 55 min. The reaction mixture is stirred at 1 20° C. for 4.5 hours until the conversion is complete.

Example 7: Symmetrical Alkylsiloxane (Reference)

In a four-necked flask equipped with stirrer, thermometer, addition funnel and reflux condenser, inerted with nitrogen, a mixture of 48.0 g (0.18 mol) 1-hexadecene and 0.1 ml of hexachloroplatinic acid, 10% w/w in isopropanol, are heated to 115° C. and 213.8 g of an α,ω-SiH functional siloxane (0.066% w/w hydrogen) are added in 1 h. The reaction mixture is stirred at 120° C. for 2 hours until the the conversion is complete.

Example 8: Two-step Synthesis of a Siloxane Composition Containing Asymmetrical Siloxanes (1. equilibration) In a four-necked flask equipped with stirrer, thermometer, addition funnel and reflux condenser, inerted with nitrogen, a mixture of 138.5 g of the symmetrical alkylsiloxane from example 6, 106.9 g of an α,ω-SiH functional siloxane (0.092% w/w hydrogen) and 0.25 g trifluoromethane sulfonic acid are stirred at 30° C. for 6 hours. 2.45 g of sodium bicarbonate are added, the mixture stirred at 30° C. for 1 hour, and filtered.

(2.hydrosilylation) In a four-necked flask equipped with stirrer, thermometer, addition funnel and reflux condenser, inerted with nitrogen, the reaction mixture and 63.44 g of an ethylene oxide-propylene oxide copolymer monoallyl ether (80 mol % propylene oxide, iodine value 50.9) are heated to 80° C. and 0.1 ml of hexachloroplatinic acid, 10% w/w in isopropanol, are added. The reaction mixture is stirred at 120° C. for 4 hours until the conversion is complete.

Example 9: Oil Compositions Containing Asymmetrical and/or Symmetrical Organopolysiloxanes The compatibility of oil spreaders was evaluated in a variety of oils.

The polysiloxane or polysiloxane blend was mixed with the oil at a concentration of 5% w/w.

The compatibility was evaluated visually after 24 hours at room temperature.

Dynamic Surface Tension Measurements were run for all oil/siloxane blends. They were evaluated on a SensaDyne 6000 with the bubble frequency calibrated at 0.5 Hz in isopropanol. Sample temperatures were 25 plus or minus 3° C. Values are reported in dynes/cm.

Description of Oils

Methylated Canola Oil=methylated canola oil with emulsifiers, Coastal Chemical, Greenville, N.C.;
Methylated Soy Oil=Kemester 226 (methylated soy bean oil), Witco, Greenwich, Conn.;
TegoSoft CT=Capric/Caprylic Triglyceride, Goldschmidt Chemical Corp., Hopewell, Va.;
Mineral Oil=Amoco 9 NF Mineral Oil, Amoco, Chicago, Ill.;
Mineral oil=Penreco Mineral Oil Drakeol 10B LT 14109 K 9014°, Penreco, Karns City, Pa.

TABLE 1

Comparison of oil compositions with asymmetrical and/or symmetrical siloxanes.

| oil | Control (no siloxane) dynes/cm | polysiloxane according example 2 compatab. | dynes/cm | polysiloxane according example 4 compatab. | dynes/cm | polysiloxane according example 6 compatab. | dynes/cm | polysiloxanes according example 4 and 6 (1:1 blend) compatab. | dynes/cm |
|---|---|---|---|---|---|---|---|---|---|
| Methylated Canola Oil | 31.1 | clear to sl. haze | 24.5 | clear | 24.5 | cloudy, separation | — | cloudy, separation | 24.5 |
| Methylated Soy Oil | 32.1 | clear | 24.4 | clear | 24.5 | clear | 24.1 | clear | 24.4 |
| TegoSoft CT | 30.8 | clear to sl. haze | 23.9 | clear | 24.0 | hazy, separation | — | hazy | 23.9 |
| White Mineral Oil #9 | 31.3 | clear, sl. separation | 25.0 | cloudy, separation | — | clear | 25.1 | cloudy, separation | 24.8 |
| Mineral Oil (Penreco) | 31.3 | clear | 25.0 | n.d. | n.d. | n.d. | n.d. | cloudy, some separation | 24.7 |

TABLE 2

Comparison of oil compositions with asymmetrical and/or symmetrical siloxanes.

| oil | Control: no siloxane dynes/cm | compatab. | polysiloxane according example 3 dynes/cm | compatab. | polysiloxane according example 5 dynes/cm | compatab. | polysiloxane according example 7 dynes/cm | compatab. | polysiloxanes: example 5 and 7 (1:1 blend) dynes/cm |
|---|---|---|---|---|---|---|---|---|---|
| Methylated Canola Oil | 31.1 | hazy, sl. separation | — | hazy | 24.1 | cloudy, separation | — | cloudy separation | 24.5 |
| Methylated Soy Oil | 32.1 | clear | 23.6 | clear | 23.9 | clear | 23.5 | cloudy, separation | 25.8 |
| TegoSoft CT | 30.8 | hazy | 23.5 | hazy | 24.0 | cloudy, separation | — | clear | 23.7 |
| White Mineral Oil #9 | 31.3 | hazy | 24.3 | cloudy, separation | — | clear | 24.5 | hazy | 23.7 |

As is usual in the art, all descriptions of polymer structures describe only the averaged mean of a broader molecular weight distribution, which is typically of a gaussian nature.

The results in table 2 demonstrate the improved compatability of compositions containing asymmetrical and symmetrical siloxanes according to example 3, compared to compositions containing only symmetrical siloxanes. The oil compositions show a low surface tension and good spreading properties.

The above description of the invention is intended to be illustrative and not limiting. Various changes or modifications in the embodiments described may occur to those skilled in the art. These can be made with out departing from the spirit or scope of the invention.

What is claimed is:

1. A method of improving the spreading of oil compositions which comprises the addition of at least one asymmetrically substituted polysiloxanes the formula

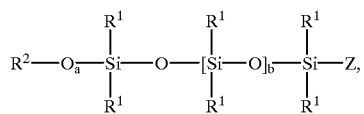

(I)

wherein

R$^1$ and R$^2$ are same or different and represent same or different linear or branched, substituted or unsubstituted, saturated or unsaturated alkyl or aryl groups with 1 to 32 carbon atoms which optionally interrupted by oxygen atoms in the hydrocarbon chains;

Z is a polyoxyalkylene radical of the structure

wherein

R$^3$ represents the same or different bivalent alkyl or aryl radicals with 1 to 30 carbon atoms, R$^4$ represents hydrogen and/or the same or different alkyl or aryl radicals with 1 to 30 carbon atoms, R$^5$ represents hydrogen and/or same or different, linear or branched alkyl, aryl or acyl radicals with 1 to 30 carbon atoms, which optionally substituted with hydroxy groups, halogens, unsubstituted or substituted alkyl, aryl, alkyloxy or aryloxy groups with 1 to 24 carbon atoms, k equals 0 or 1,
equals 0 or 1,
m equals 0 or 1,
n equals 2 or 4,
o equals values from 1 to 100;
a equals 0 or 1, and
b equals 0 to 200.

2. An oil composition having improved spreading properties which comprises 99.9% to 50% by weight of one or several oils; and 0.01% to 50% by weight of an organosilicone composition comprising asymmetrically substituted polysiloxanes according to formula (I)

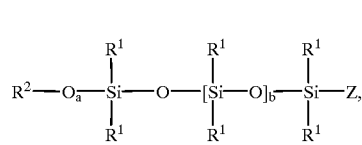

(I)

wherein

R$^1$ and R$^2$ are same or different and represent same or different linear or branched, substituted or unsubstituted, saturated or unsaturated alkyl or aryl groups with 1 to 32 carbon atoms which optionally interrupted by oxygen atoms in the hydrocarbon chains;

Z is a polyoxyalkylene radical of the structure

wherein

R$^3$ represents the same or different bivalent alkyl or aryl radicals with 1 to 30 carbon atoms, R$^4$ represents hydrogen and/or the same or different alkyl or aryl radicals with 1 to 30 carbon atoms, R$^5$ represents hydrogen and/or same or different, linear or branched alkyl, aryl or acyl radicals with 1 to 30 carbon atoms, which optionally substituted with hydroxy groups, halogens, unsubstituted or halogensubstituted alkyl, aryl, alkyloxy or aryloxy groups with 1 to 24 carbon atoms, k equals 0 or 1,
l equals 0 or 1,
m equals 0 or 1,
n equals 2 or 4, o equals values from 1 to 100;
a equals 0 or 1, and
b equals 0 to 200;

and, optionally, one or several symmetrical polysiloxanes according to the formula (II)

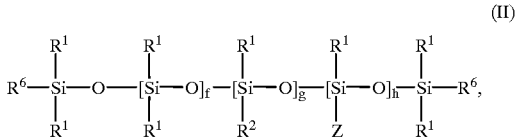
(II)

wherein $R^1$, $R^2$ and Z assume the meaning defined above, $R^6$ assumes the meaning of $R^2$ or that of Z, f, g and h are 0 to 200, and which optionally contain branching units of the structure

[$R^6SiO_{3/2}$].

3. A composition according to claim 2, wherein $R^1$ 1 is methyl, a equals 0 and b equals 10 to 100, $R^2$ are same or different alkyl groups with 10 to 18 carbon atoms, $R^3$ represents propyl, k equals 1, l equals 1, m equals 0 or 1, n equals 2, o equals 5 to 100, $R^4$ is from the group of hydrogen, methyl, ethyl or phenyl, residues $R^5$ are from the group of hydrogen, methyl, acetyl or alkylsubstituted phenyl, $R^6$ assumes the meaning of $R^2$ or Z, f equals 5 to 80 and g and h are 0.

4. A composition according to claim 2, wherein the oil is a vegetable oil or a methylated vegetable oil.

5. A composition according to claim 2, where the organosilicone composition does not contain more than 40% by weight of each single symmetrical polysiloxane of formula (II).

6. A composition according to claim 2 which comprises 99.9% to 90% by weight of one or several oils; and 0.01% to 10% by weight of an organosilicone composition comprising 30% to 100% by weight of asymmetrically substituted polysiloxanes; and 0% to 70% of symmetrical organosiloxanes of formula (II).

7. A composition according to claim 2 which comprises 99.9% to 90% by weight of one or several oils; and 0.01% to 10% by weight of an organosilicone composition comprising 90% to 100% by weight of asymmetrically substituted polysiloxanes; and 0% to 10% by weight of one or several organosiloxanes of formula (II).

8. A composition according to claim 2 which comprises 99.9% to 90% by weight of one or several oils; and 0.01% to 10% of an organosilicone composition comprising 40% to 60% by weight of asymmetrically substituted polysiloxanes; and 60% to 40% by weight of organosiloxanes of formula (II).

9. A herbicidal composition exhibiting improved spreading properties which comprises a composition according to claim 2 and an effective amount of a herbicide.

10. A composition according to claim 9 in which the herbicide is glyphosate.

11. A pesticidal composition exhibiting improved spreading properties which comprises a composition according to claim 2 and an effective amount of a pesticide.

12. A method of combatting pests which comprises administering an effective amount of oil compositions according to claim 2 to the pests.

13. A preparation for use in personal care or pharmaceutical applications which comprises a composition according to claim 2 and effective amounts of pharmaceutically or cosmetically active ingredients.

14. A preparation for use in agricultural and in industrial applications, or as surface-active agents in the paper, plastics and metallurgical industry which comprises a composition according to claim 2 and effective amounts of active ingredients.

* * * * *